Figure 1:
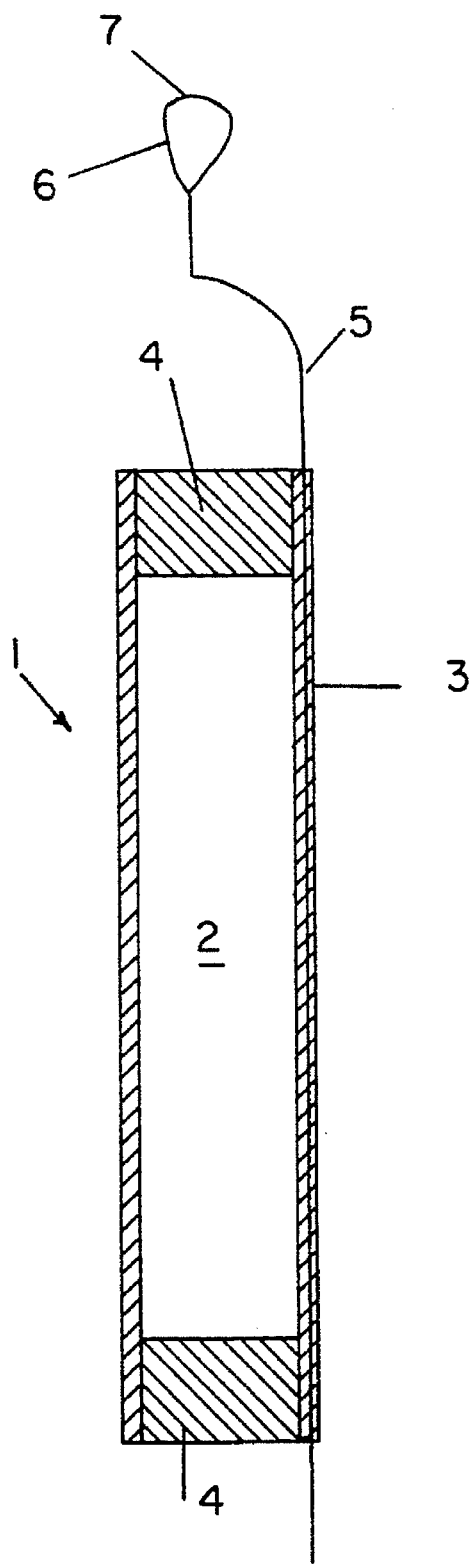

United States Patent [19]
Lehtinen

[11] Patent Number: 5,626,148
[45] Date of Patent: May 6, 1997

[54] DEVICE FOR INTRAUTERINE USE

[75] Inventor: Matti Lehtinen, Kaarina, Finland

[73] Assignee: Leiras Oy, Turku, Finland

[21] Appl. No.: 167,792

[22] PCT Filed: Jun. 17, 1992

[86] PCT No.: PCT/FI92/00189

§ 371 Date: Feb. 22, 1994

§ 102(e) Date: Feb. 22, 1994

[87] PCT Pub. No.: WO93/00055

PCT Pub. Date: Jan. 7, 1993

[30] Foreign Application Priority Data

Jun. 20, 1991 [FI] Finland ................................ 913025

[51] Int. Cl.⁶ .................................. A61F 6/06; A61F 6/14
[52] U.S. Cl. ........................ 128/830; 128/832; 128/839
[58] Field of Search ........................................ 128/830–841

[56] References Cited

U.S. PATENT DOCUMENTS 3,396,819 8/1968 Zaffaroni et al. .
3,954,103 5/1976 Garcia-Roel ............................ 128/839
4,708,134 11/1987 Wildemeersch .
5,303,717 4/1994 Wildemeersch ........................ 128/830

FOREIGN PATENT DOCUMENTS 0082894 7/1983 European Pat. Off. .

OTHER PUBLICATIONS

International Publication WO 91/00714 published 24 Jan. 1991.

Primary Examiner—Michael A. Brown
Attorney, Agent, or Firm—Birch, Stewart, Kolasch & Birch, LLP

[57] ABSTRACT

Device for intrauterine use comprising means (7, 8) for attaching the device to the interior wall of the uterus, as well as a member (1) releasing active agent and connected to the said attachment means. The invention is characterized in that the active agent releasing member (1) is in the form of a closed container enclosing the active agent, the walls of the container being at least partly permeable to the active agent.

3 Claims, 1 Drawing Sheet

U.S. Patent      May 6, 1997      5,626,148

DEVICE FOR INTRAUTERINE USE

The object of the present invention is a device for intrauterine use comprising means for attaching the device to the interior wall of the uterus, as well as an active agent releasing member connected to the said attachment means.

Various devices for intrauterine application are widely used for contraceptive purposes. Contraceptives, i.a. releasing copper ions and generally of T-shape, so called spiral-IUDs, one variant of which is also hormone releasing, have today gained extensive use. These contraceptives are fitted by means of an insertion tube into the uterus, wherein they more or less adapt to the interior space of the uterus. Although the preventive effect of these contraceptives generally speaking is good, they have some disadvantages. One such disadvantage is the mechanical strain of the T-hook on the walls of the uterus, which may lead to the breaking of the wall structure, or even to the hook growing into the wall.

Also contraceptive devices have been proposed in the literature which are attached to the wall of the uterus, usually its back wall. In this case the contraceptive need not be hook-shaped and there is no risk of the contraceptive discharging from the uterus. One such solution is disclosed in the U.S. Pat. No. 4,708,134, which comprises successive hollow tubular bodies, especially of copper, attached to a thread, which tubular construction can be attached to the inner wall of the uterus by means of a hook or a knot connected with the thread. Another device to be attached with a hook to the wall of the uterus is known from the EP-patent specification A 0100924, according to which a string of copper beads, either in the form of a single strand or a loop, is attached to a hook. This device is fitted in its place with a special, relatively large insertion device, which, when turned, makes the upper end of the hook correspondingly turn and attach to the wall of the uterus. Both devices are complicated to their construction and the latter especially to its way of insertion, which substantially decreases their application possibilities.

From the WO-publication WO90/05507 a device for attachment to the uterus wall is known, wherein the active agent releasing member is of polymer fibres in the form of individual fibre strands or fibre loops. Although the detailed structure of the fibres has not been described in the said publication, it is evident that they are formed of a polymer permeable to active agent, e.g. steroids, into the matrix of which the active agent is distributed and wherefrom it diffuses out. Such matrix-active agent systems do, however, exhibit some disadvantages, especially as regards the release profile of the active agent. The release rate of the active agent is dependant on both the concentration of the active agent in the matrix, as well as on the surface area of the matrix body. When the matrix is degraded due to the conditions within the uterus and the release of active agent, the permeability of the active agent and thus the release rate increases. As this process cannot be controlled, the release of active agent will be uneven and thus unreliable.

According to the invention a device has now been developed which eliminates the afore mentioned disadvantages and which allows for a reliable and controlled release of active agent into the uterus. Thus the device according to the invention is characterized in that the active agent releasing member is in the form of a closed container enclosing the active agent, at least a part of the walls of the container being permeable to the active agent.

The device according to the invention is advantageously in the form of a cylinder or a capsule, wherein the walls of the cylinder or capsule are permeable to the active agent. A material suitable for the walls or wall parts is a silicone polymer. A suitable container for the purpose of the invention is obtained by cutting tubular pieces of a suitable length from a thin silicone tube, closing one end thereof by gluing, for example using a silicone glue, filling the tube with the desired active agent, which advantageously is a mixture of active agent and silicone polymer, but which may also be in the form of a liquid or a powder, and subsequently closing the other end of the cylinder in a corresponding manner. Typically such a tubular container has a diameter of at the most a few millimeters, and a length of a few centimeters.

The container is in a suitable manner connected to attachment means for attachment to the uterus wall, for example by a thin thread, which is, for example, a polymer or metal suitable for the purpose. The part to be attached to the wall of the uterus itself may be a knot formed in the thread, for example in a loop thereof, or it may be a hook-shaped member fastened to the thread.

For the purpose of removing the container, a thread of sufficient length is suitably attached to the container so that it extends beyond the cervix when the device is attached to the uterus wall.

The device according to the invention may be inserted in a known manner for example by engaging the loop or hook with a thin stick the end of which is provided with suitably shaped gripping means, such as a small hook, and by inserting the device with the stick, within a suitable hollow insertion tube, through the cervix into the uterus and by attaching the device to the uterus wall. Thereafter the stick is released from the device and the stick and insertion tube are removed.

One and the same thread may be used both for connecting the container to the attachment means, and as a thread for removal. When the container is cylindrical, this can be achieved, for example, by threading the thread with a suitable means through the longitudinal wall structure of the cylinder, substantially along its whole length, or correspondingly through the end wall or walls in the transverse direction of the cylinder. The attachment means is then connected to one end of the thread, and the other end functions as a thread for removal of the device.

With the device according to the invention it is possible to controllably release into the uterus various active agents, especially various hormones, typically estrogens and/or progestins. The device according to the invention is therefore suited especially well for contraceptive purposes, but naturally it may be used also for therapeutic purposes, such as, for example, to treat postmenopausal problems. The use of the device according to the invention for contraceptive and therapeutic purposes thus also forms an object of the invention.

The release rate of the active agent is dependant on i.a. the wall surface area of the container releasing active agent, as well as on the thickness of the wall structure. When using cylindrical capsules of the afore mentioned type, it is possible, when the other parameters of the capsules remain constant, to accurately regulate the duration of the treatment by choosing a capsule of suitable length, or by coupling together in a row several capsules.

The device according to the invention has several advantages. With respect to the said known devices it is simpler to manufacture, and is more dependable to its release profile. Compared to the T-contraceptive widely in use it gives rise to clearly less mechanical strain in the uterus.

It is also advantageous when compared to the known implant capsules to be installed under the skin, especially for contraceptive use. Firstly, it is both easier to insert as well as easier to remove than an implanted capsule, the implantation of which always requires a small surgical procedure with associated disadvantages. When in intrauterine use, the dose of the active agent is also smaller than that of a systemically administered active agent, even only ¼ thereof, as the effect is directed directly on the uterus and its mucous membranes. As the dosage can be reduced, also the possible side effects are reduced.

In the following reference is made to the appended drawing, wherein as an example two embodiments of the invention are shown.

Figure 2:
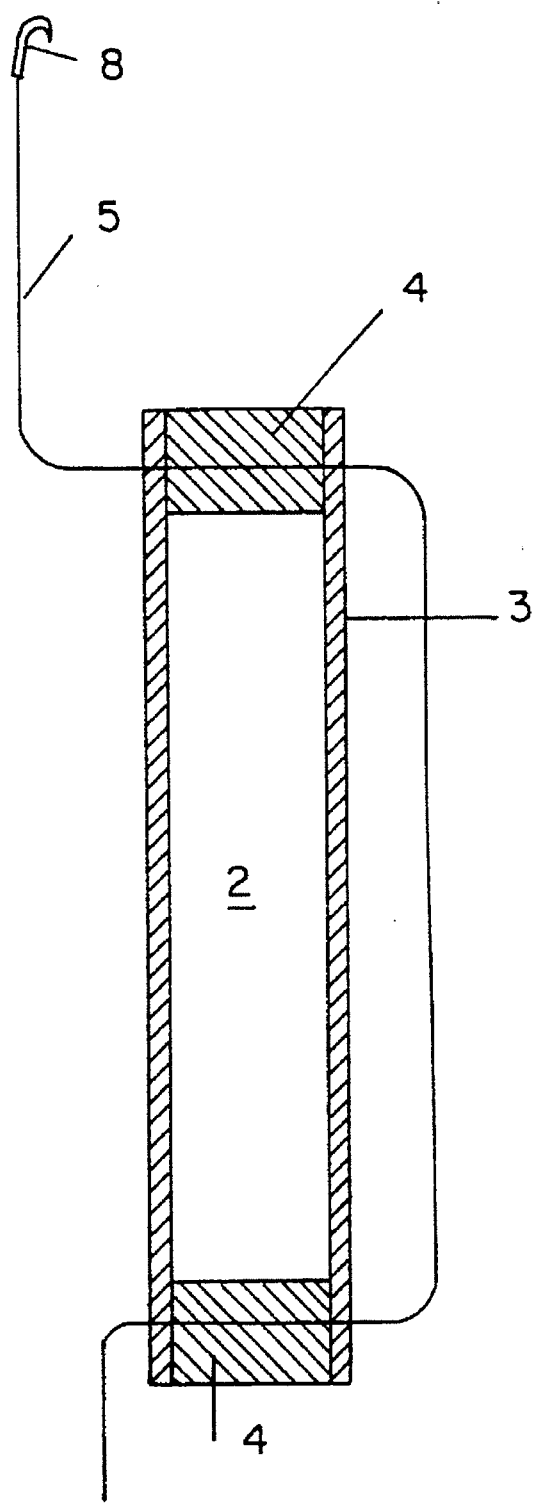

FIG. 1 shows a container of capsular form according to the invention, and FIG. 2 an alternative attachment system fox the container according to the FIG. 1. In both figures the same reference numerals are used for corresponding parts.

In the embodiment of FIGS. 1 and 2 the capsule made from a silicone polymer tube is as a whole designated with the reference numeral 1 and it encloses the active agent 2. The longitudinal walls of the capsule are given the reference numeral 3, and the body member is made from the silicone polymer tube by cutting thereof a piece of suitable length. The ends of the tube closed with silicone glue are given the reference numeral 4. The capsule is with a thread 5 connected to attachment means, which according to the FIG. 1 is comprised of a loop 6 and a knot 7 made therein. In the construction of FIG. 2, the attachment means is a hook 8. Both the knot 7 and the hook 8 are designed to be attached to the wall of the uterus, preferably its back wall. In the embodiment shown, one end of the thread 5 is intended to be connected to the attachment means, and the other end for removal of the capsule from the uterus. In order to obtain a sufficiently strong connection, the thread 5 is in the example shown (FIG. 1) threaded, for example, with a thin needle through the side wall 3 of the capsule which has been suitably softened, such as with a solvent, in its longitudinal direction, or in the alternative embodiment shown in the FIG. 2, through the both end wall parts 4 of the capsule. It is of course possible to use different lengths of thread for the attachment means 7 and 8, and for removing the capsule, respectively, by connecting each end part of the capsule to its respective length of thread in a suitable manner.

I claim:

1. A device for intrauterine use comprising attachment means selected from the group consisting of a knot or a hook attachable to the interior wall of the uterus which is connected to an active agent releasing member in the form of a capsule shaped container having end parts and having walls which are permeable to the active agent, said attachment means being connected to said capsule shaped container by a thread threaded in the transverse direction though the end parts of said capsule shaped container.

2. Device according to claim 1, characterized in that the wall of the container permeable to the active agent is made of a silicone polymer sheet or film.

3. Device according to claim 1, characterized in that the active agent is estrogen and/or progestin.

* * * * *